(12) United States Patent
Takemoto et al.

(10) Patent No.: US 9,669,044 B2
(45) Date of Patent: Jun. 6, 2017

(54) AMINOGLYCOSIDE AND AZOLE COMPOSITIONS AND METHODS

(71) Applicants: Jon Y. Takemoto, North Logan, UT (US); Cheng-wei Tom Chang, Logan, UT (US); Sanjib K. Shrestha, Lexington, KY (US); Michelle Grilley, Logan, UT (US)

(72) Inventors: Jon Y. Takemoto, North Logan, UT (US); Cheng-wei Tom Chang, Logan, UT (US); Sanjib K. Shrestha, Lexington, KY (US); Michelle Grilley, Logan, UT (US)

(73) Assignee: Utah State University, Logan, UT (US)

(*) Notice: Subject to any disclaimer, the term of this patent is extended or adjusted under 35 U.S.C. 154(b) by 0 days.

(21) Appl. No.: 14/281,659

(22) Filed: May 19, 2014

(65) Prior Publication Data

US 2014/0256665 A1 Sep. 11, 2014

Related U.S. Application Data

(63) Continuation-in-part of application No. 13/316,720, filed on Dec. 12, 2011, now Pat. No. 8,865,665.

(60) Provisional application No. 61/824,847, filed on May 17, 2013, provisional application No. 61/422,983, filed on Dec. 14, 2010.

(51) Int. Cl.
| | |
|---|---|
| *A61K 31/7036* | (2006.01) |
| *A61K 31/496* | (2006.01) |
| *A61K 31/4196* | (2006.01) |
| *A61K 31/506* | (2006.01) |
| *A61K 31/415* | (2006.01) |
| *A61K 31/365* | (2006.01) |
| *A01N 43/16* | (2006.01) |

(52) U.S. Cl.
CPC .......... *A61K 31/7036* (2013.01); *A01N 43/16* (2013.01); *A61K 31/365* (2013.01); *A61K 31/415* (2013.01); *A61K 31/4196* (2013.01); *A61K 31/496* (2013.01); *A61K 31/506* (2013.01)

(58) Field of Classification Search
None
See application file for complete search history.

(56) References Cited

U.S. PATENT DOCUMENTS

| | | | |
|---|---|---|---|
| 4,279,997 A | 7/1981 | Oka et al. | |
| 4,493,831 A | 1/1985 | Takya et al. | |
| 5,039,666 A | 8/1991 | Novick | |
| 8,865,665 B2 | 10/2014 | Cheng | |
| 2003/0091510 A1 | 5/2003 | Ponikau | |
| 2005/0159369 A1* | 7/2005 | Lane | A61K 31/00 514/28 |
| 2008/0220103 A1* | 9/2008 | Birnbaum | A01N 25/00 424/735 |
| 2011/0130357 A1 | 6/2011 | Cheng | |
| 2011/0190233 A1 | 8/2011 | Kett et al. | |
| 2012/0316125 A1 | 12/2012 | Chang et al. | |

FOREIGN PATENT DOCUMENTS

| | | |
|---|---|---|
| CN | 101481397 | 7/2009 |
| WO | 2004050677 A1 | 6/2004 |
| WO | 2005116041 A2 | 12/2005 |
| WO | 2009152202 A2 | 12/2009 |

OTHER PUBLICATIONS

Sheehan, D. J., Hitchcock, C. A., & Sibley, C. M. (1999). Current and emerging azole antifungal agents. Clinical microbiology reviews, 12(1), 40-79.*
Definition of "compound" and "composition" in Grant and Hackh's chemical dictionary, 5th Ed. McGraw Hill. 1987.p. 148. ISBN 0-07-024067-1.*
Dozzo, P., & Moser, H. E. (2010). New aminoglycoside antibiotics. Expert opinion on therapeutic patents, 20(10), 1321-1341.*
"Prevention" in Glossary of medical education terms: Parts 1-7. Wojtczak, A., Ed. Medical Teacher. vol. 24, Nos. 2-6 and vol. 25, No. 1&2. 2002.*
Chang, et al., Antibacterial to antifungal conversion of neamine aminoglycosides through alkyl modification. Strategy for reviving old drugs into agrofungicides, 63:11 The Journal of Antibiotics 667-672, Oct. 6, 2010, Nature Publishing Group.
Schepdael et al., New Derivatives of Kanamycin B Obtained by Modifications and Substitutions in Position 6".1., Synthesis and Microbiological Evaluation, 34 J. Medicinal Chemistry, 34(4), 1468-1475, 1991.
Wang et al., Glycodiversification for the Optimization of the Kanamycin Class Aminoglycosides, 48 J. Medicinal Chemistry 6271-6285, Sep. 2, 2005.
Wang et al., Design, Chemical Synthesis, and Antibacterial Activity of Kanamycin and Neomycin Class Aminoglycoside Antibiotics (Ch. 4, pp. 141-180), In: Arya, D. P (2007) Aminglycoside antibiotics: from chemical biology to drug discovery (vol. 5) Wiley.com.
Woo et al., Synergism between fungal enzymes and bacterial antibiotics may enhance biocontrol, Antonie van Leeuwenhoek 81: 353-356, 2002, Netherlands.
PCT/US2011/064481; filed Dec. 12, 2011; Utah State University et al; International Search Report Mailing date Jun. 27, 2013.
Le et al. Novel kanamycin A derivative, and preparation and use thereof, CN 101481397 A, Jul. 15, 2009, machine translation, Retrieved on Jul. 14, 2015 from http://worldwide.espacenet.com.

(Continued)

*Primary Examiner* — Shaojia Anna Jiang
*Assistant Examiner* — Dale R Miller

(57) ABSTRACT

The present invention relates to novel fungicidal compound including an aminoglycoside analog having certain substituents at the 6 position of ring III that exhibit improved antifungal activity but possess minimal antibacterial properties in combination with fungicidal azoles. The aminoglycoside compounds are analogues of kanamycin A. Also provided are methods of synthesizing and methods of using the compounds of the present invention. The compounds of the present invention are useful in treating or preventing fungal disease.

20 Claims, 4 Drawing Sheets

(56) References Cited

OTHER PUBLICATIONS

Rosenbohm, et al., Parallel Synthesis of a Small Library of Novel Aminoglycoside Analogs Based on 2-amino-2-deoxy-D-glucose and D-ribose scaffolds, Tetrahedron, 2001, pp. 6277-6287, vol. 57.
Notification of Transmittal of the International Search Report and the Written Opinion of the International Searching Authority, or the Declaration, dated Nov. 4, 2014 for PCT/US2014/038649, International filing date of May 19, 2014.

* cited by examiner

AMINOGLYCOSIDE AND AZOLE COMPOSITIONS AND METHODS

RELATED APPLICATIONS

This application claims priority to U.S. Provisional Application No. 61/824,847, filed May 17, 2013 and is a continuation-in-part application to U.S. patent application Ser. No. 13/316,720, filed Dec. 12, 2011, which claims the benefit of U.S. Provisional Application No. 61/422,983, filed Dec. 14, 2010.

This application is related to U.S. patent application Ser. No. 12/968,052, filed Dec. 14, 2010, which is a continuation-in-part application of International Patent Application PCT/US2009/046827, filed Jun. 10, 2009, which in turn claims priority to U.S. Provisional Application No. 61/060,661, filed Jun. 11, 2008, each of which applications are hereby incorporated herein by reference in their entirety.

TECHNICAL FIELD

The present disclosure relates to active chemical combinations. More particularly, the present disclosure relates to aminoglycoside and azole combinations and their antibiotic activities.

BACKGROUND

Aminoglycoside antibiotics have been commonly used as a medical treatment against infectious diseases for over 60 years, although the prevalence of aminoglycoside resistant bacteria has significantly reduced their effectiveness. Aminoglycosides have two or more amino sugars bound to an aminocyclitol ring through glycosidic bonds. Naturally occurring aminoglycosides (produced by *Actinomycetes*) are widely used as antibiotics against bacterial infections of animals and humans. These include the well-known antibiotics kanamycin, streptomycin, and neomycin. Aminoglycoside antibiotics are believed to act on the bacterial protein synthesis machinery, leading to the formation of defective cell proteins.

In medicine, fungal diseases have emerged over the last 25 years as a major public health problem. Among the prominent reasons for this increase are the lack of efficacious antifungal agents, increases in immunocompromised conditions (e.g., organ transplants and HIV/AIDS), and widespread resistance to the most commonly used antifungals. The strongest medically used antifungal agent, amphotericin B, is an effective medication, but is also highly toxic to patients. The toxicity levels of the available antifungal medications are a common concern for medical practitioners. U.S. Pat. No. 5,039,666 to Novick, Jr. (1991) shows an aminoglycoside compound "gentamicin" having reduced nephrotoxicity induced by the aminoglycoside. Other common antifungal medications are used to treat infections such as athlete's foot, ringworm, candidiasis (thrush) and serious systemic infections such as cryptococcal meningitis, and others.

In agriculture, the control of crop diseases by direct application of biocides remains the most effective and most widely used strategy. Nevertheless, concerns with inconsistent and declining effectiveness, environmental impacts, animal/human toxicity, and costs continue to challenge the use of existing biocides. Traditionally, aminoglycosides have been developed and used as antibiotics against bacteria. A recent report, however, suggests inhibition of plant pathogenic fungi (particularly by paramomycin) by traditional and natural aminoglycosides. One specific example of a crop pathogen is *Fusarium graminearum*, the most common causative agent of head blight disease in wheat and barley in North America. Infection with *F. graminearum* is difficult to predict and can result in catastrophic crop loss.

Kanamycin is a known aminoglycoside antibiotic. The antibiotic function of kanamycin may be related to its ability to affect the 30S ribosomal subunit of bacteria, causing frameshift mutations or preventing the translation of RNA. Either frameshift mutations or a lack of RNA translation can lead to a reduction or absence of bacterial protein synthesis and, ultimately, to bacterial death. Unfortunately, kanamycin has been rendered all but obsolete for clinical use due to the emergence of resistant bacteria.

Clearly there exists a need for novel antimicrobials to address the problems of resistant bacteria and fungi, both in human medicine and in crop disease. There is also a clear need for novel antimicrobials, especially antifungals, with reduced toxicity. Furthermore, it would be desirable for new antimicrobial compounds to be selective against either bacteria or fungi, so treatment for one of either bacterial or fungal disease does not contribute to the buildup of antimicrobial resistance in the other. Selective antimicrobial activity is especially desirable for antifungals used to treat crop disease, such as *Fusarium* head blight, due to the possibly large amounts of antimicrobial agent released into the environment when crops are treated. The present invention provides for novel aminoglycoside antimicrobials that are effective, have relatively low levels of toxicity, and are selective against fungal pathogens.

SUMMARY

The present disclosure in aspects and embodiments addresses these various needs and problems by providing an azole-aminoglycoside compound with biocidal effects.

In some embodiments, the fungicidal compound comprises an aminoglycoside compound, or salt thereof having the formula:

Formula I

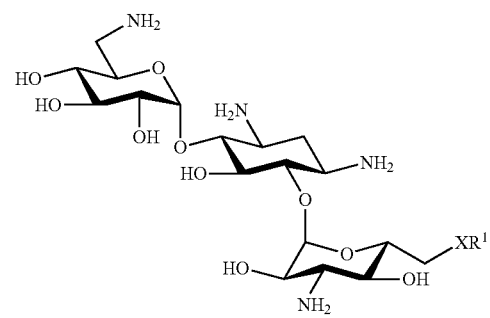

wherein:
X is a member selected from the group consisting of O, S, and $NR^2$;
$R^1$ is a member selected from the group consisting of $R^3$, $C(O)OR^3$, $NH(CO)R^3$, $S(O)_2R^3$, $S(O)_2R^4$, $S(O)R^3$, $P(O)_2R^3$, $C(O)R^3$, and phenyl, wherein phenyl groups may be $C_1$ to $C_6$ alkyl substituted;
$R^2$ is H or $C_1$ to $C_6$ alkyl;
$R^3$ is a straight or branched chain $C_4$ to $C_{12}$ alkyl group;
$R^4$ is phenyl or $C_1$ to $C_6$ alkyl substituted phenyl; and an azole.

The aminoglycoside analogs are derived from the parent molecule of kanamycin A.

It is also an object of the present invention to provide novel aminoglycoside analog compounds of Formula I having improved antimicrobial and particularly antifungal properties when combined with selected azole compounds that also exhibit biocidal, antimicrobial, or antifungal effects.

A still further object of the present invention is to provide method of synthesizing aminoglycoside analog compounds of Formula I. Yet another object of the present invention is to provide methods of using aminoglycoside analog compounds of Formula I as biocides having improved fungicidal activity.

Without limiting the invention to any particular method of use, the compounds of the present invention unexpectedly demonstrate increased specificity for fungal pathogens and a lack of activity against some common bacterial pathogens. In addition, the synergistic effects of the added azole exhibit drastically improved biocidal effects.

Other synthetic aminoglycosides and the natural aminoglycosides are either solely bacteriocidal or both bacteriocidal and fungicidal. As a result of its unexpected specificity for fungal pathogens, the compounds of the present invention provide for advantageous treatment of fungal pathogens by not promoting resistance of pathogenic bacteria to traditional aminoglycosides and by not harming or eliminating nonpathogenic bacteria. Various embodiments of the present invention, as well as examples for a method of synthesizing and methods of using the compound of the present invention, are discussed below.

DETAILED DESCRIPTION

Figure 1:
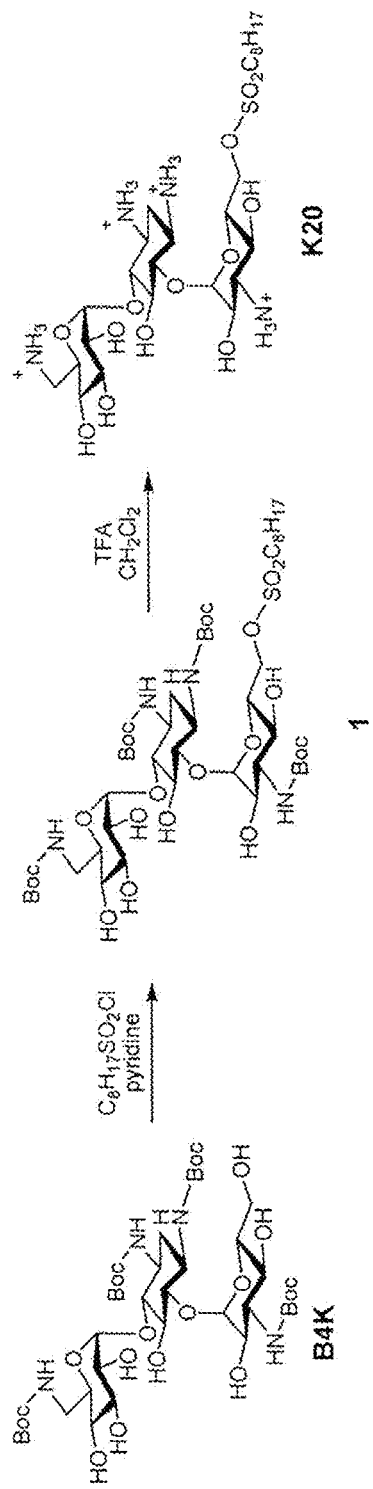
FIG. 1 illustrates an exemplary method to synthesize an exemplary aminoglycoside.

The present disclosure covers compositions, kits, reagents, and associated methods for active compounds that include aminoglycosides and azoles. In the following description, numerous specific details are provided for a thorough understanding of specific preferred embodiments. However, those skilled in the art will recognize that embodiments can be practiced without one or more of the specific details, or with other methods, components, materials, etc. In some cases, well-known structures, materials, or operations are not shown or described in detail in order to avoid obscuring aspects of the preferred embodiments. Furthermore, the described features, structures, or characteristics may be combined in any suitable manner in a variety of alternative embodiments. Thus, the following more detailed description of the embodiments of the present invention, as illustrated in some aspects in the drawings, is not intended to limit the scope of the invention, but is merely representative of the various embodiments of the invention.

In this specification and the claims that follow, singular forms such as "a," "an," and "the" include plural forms unless the content clearly dictates otherwise. All ranges disclosed herein include, unless specifically indicated, all endpoints and intermediate values. In addition, "optional" or "optionally" refer, for example, to instances in which subsequently described circumstance may or may not occur, and include instances in which the circumstance occurs and instances in which the circumstance does not occur. The terms "one or more" and "at least one" refer, for example, to instances in which one of the subsequently described circumstances occurs, and to instances in which more than one of the subsequently described circumstances occurs.

A. Definitions

Before discussing the present invention in further details, the following terms, when and if used, and conventions will first be defined:

Host: The term "host" is defined herein as any living organism infected or at least somewhat likely of being infected by a fungal pathogen, where said pathogen and any infection caused by said pathogen, or potential infection caused by said pathogen, are susceptible to treatment with one or more of the compounds of Formula I as claimed herein, where said treatment is likely to result in the elimination, avoidance, or alleviation of the infection caused by said pathogen.

The following is in reference to Formula I, FIG. 1, Table 1, Table 2 and elsewhere: Unless otherwise designated in Formula I, FIG. 2, and Tables 1 and 2, all carbon chains are straight chains, i.e. are n-alkyl or n-alkylene groups and not are branched chains.

When X is O and $R^1$ is $C(O)C_7H_{15}$ the compound is designated herein as K05 and is named 6"-O-octanoylkanamycin A.

When X is O and $R^1$ is $C(O)C_9H_{19}$ the compound is designated herein as K07 and is named 6"-O-decanoylkanamycin A.

When X is NH and $R^1$ is $C_8H_{17}$ the compound is designated herein as K17 and is named 6"-deoxy-6"-octylaminokanamycin A.

When X is S and $R^1$ is $C_8H_{17}$ the compound is designated herein as K18 and is named 6"-deoxy-6"octylthiokanamycin A.

When X is O and $R^1$ is $S(O)_2$p-tolyl the compound is designated herein as K19 and is named 6"-O-toluenesulfonylkanamycin A.

When X is O and $R^1$ is $S(O)_2C_8H_{17}$ the compound is designated herein as K20 and is named 6"-O-octanesulfonylkanamycin A.

When X is O and $R^1$ is $S(O)_2C_6H_{13}$ the compound is designated herein as K22 and is named 6"-O-hexanesulfonylkanamycin A.

For comparative purposes Kanamycin A has the structure:

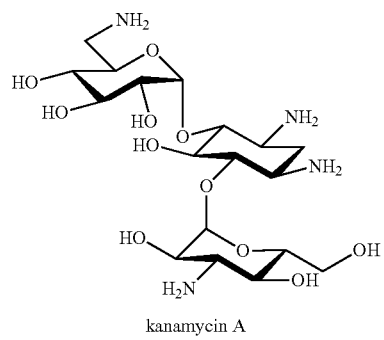

kanamycin A

Some or all of the following definitions may also be utilized throughout this disclosure.

Fungal Infection: The term "fungal infection" is defined herein as an association of a fungal organism with a host, whether said association is actual or potential. For example, an actual associate occurs when a fungi is physically present on or within a host. Examples of potential associations include fungi on or within the environment surrounding a host, where the fungi is at least somewhat likely to be actively or passively transferred to the host. Without wishing to further limit the type of associations between a fungal organism and host, examples of the association of the fungal organism with the host include biological associations that may be pathogenic or non-pathogenic, parasitic or non-parasitic, symbiotic or non-symbiotic, mutualistic or non-mutualistic, commensal, naturally occurring or man-made, or any other biological interaction.

Host in need thereof: The phrase "host in need thereof" is defined herein as any host associated or potentially associated with a fungal organism, where said host may actually or potentially benefit from elimination, prevention, or alleviation of a fungal infection.

Fusarium Head Blight: The phrase "*fusarium* head blight" is defined herein as any fungal disease caused by the fungus *Fusarium graminearum*.

Surfactant: The term "surfactant" is used to indicate the common laboratory surfactant $C_{58}H_{114}O_{26}$. All uses of the term "surfactant" refer to $C_{58}H_{114}O_{26}$, unless otherwise indicated.

Prophylactically: The term "prophylactically" is used herein to refer to the administration of an antimicrobial compound for the prevention of disease.

N/A: As used herein to describe data points, the abbreviation "N/A" means not tested.

Adjuvant: The term "adjuvant" is defined herein as a substance that helps and enhances the pharmacological effect of a drug or increases the ability of an antigen to stimulate the immune system.

Excipient: The term "excipient" is defined herein as an inactive substance used as a carrier for the active ingredients of a medication.

Diluent: The term "diluent" is defined herein as any liquid or solid material used to dilute or carry an active ingredient.

Antifungal Amount or antifungal effective: Unless otherwise specified, the phrases "antifungal amount" or "Antifungal Effective" are used herein to describe an amount of an antifungal agent sufficient to reduce, eliminate, or alleviate a fungal infection or the symptoms of a fungal infection on or within a host.

MIC: The term MIC means the minimal inhibitory concentration or lowest concentration of an antimicrobial that will inhibit the visible growth of a microorganism after 24, 48, or 72 hours of incubation.

Admixed: The term "admixed" is used herein to describe a chemical or compound in a mixture or combination with other chemicals or compounds.

Administering: The term "administering" is defined herein to describe the act of providing, exposing, treating, or in any way physically supplying or applying a chemical or compound to any living organism or inanimate object associated with a living organism, where said organism will actually or potentially benefit for exposure, treatment, supplying or applying of said chemical or compound.

Topical: The term "topical" is defined herein as pertaining to the surface of a body part, surface part of a plant, or surface of an inanimate object or composition, such as soil. For example, in medicine, a topical medication is applied to body surfaces such as the skin or mucous membranes, for example throat, eyes and ears.

Carrier: The term "carrier" is defined herein as any substance that serves to improve the delivery and the effectiveness of a drug or antimicrobial agent and is inclusive of excipients as defined above. Examples include: microspheres made of biodegradable polymer poly(lactic-co-glycolic) acid, albumin microspheres, synthetic polymers (soluble), protein-DNA complexes, protein conjugates, erythrocytes, nanoparticles, and liposomes.

Grain head: The phrase "grain head" as used herein is meant to include both small and large grains.

Warm-blooded animal: Used herein the phrase "warm-blooded animal" means an animal characterized by the maintaining of a relatively constant and warm body temperature independent of environmental temperature; homeothermic.

Certain terms in this application are to be interpreted as commonly used in the technical fields of medicine, antimicrobials, and crop disease, as indicated by the context of their use. These terms include spray nozzle, droplet, therapeutically, exterior, spraying, topical, treatment, and prevention.

PDB-CA: The term PDB-CA refers to potato dextrose broth+casamino acids medium used for fungal growth and as diluent in MIC tests. To make 1L of PDB-CA, 200 g of diced fresh potatoes were boiled in 500 mL of distilled water for 30 min. The broth was filtered through 2 layers of cheesecloth, and the volume was brought up to 1 L. After addition of 20 g of glucose (2%, w/v) and 4 g of casamino acid (0.4%, w/v), the mixture was stirred with a magnetic bar until all solids were dissolved. The pH was adjusted with HCl and NaOH to 5.1. Then, the medium was sterilized by autoclaving for 30 min.

PDA-CA: The term PDA-CA refers to a solid growth medium composed of 2% agar dissolved in PDB-CA. The mixture was sterilized by autoclaving for 30 min, poured into sterile Petri dish plates, and solidified in the plates upon cooling to room temperature.

RPMI 1640: The term RPMI 1640 refers to a chemically defined cell growth medium composed of twenty amino acids, eleven vitamins, calcium nitrate ($Ca(NO_3)_2$ $4H_2O$), magnesium sulfate ($MgSO_4$) (anhyd.), potassium chloride (KCl), sodium chloride (NaCl), sodium phosphate dibasic ($Na_2HPO_4$) anhydrous, dextrose, glutathione (reduced) and buffered to a pH of 7.0 with 0.165 M morpholinepropanesulfonic acid (MOPS) buffer (as described by Moore, G. E., Gerner, R. E. and Franklin, H. A. (1967) J. Amer. Med. Assoc. 199:519). For the studies described herein RPMI 1640 was purchased from Sigma-Aldrich Chemical Co., St. Louis, Mo., USA).

B. Aminoglycosides

The present invention relates to antimicrobial compounds comprising aminoglycosides and azoles. Exemplary aminoglycosides include the compound of Formula I as follows:

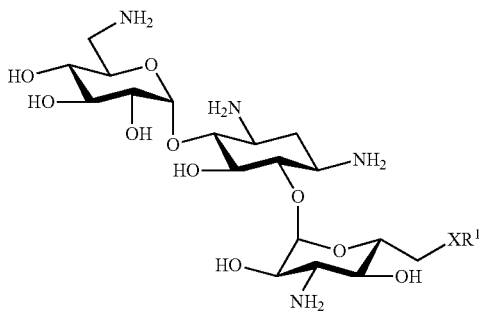

Formula I wherein:

X is a member selected from the group consisting of O, S, and $NR^2$;

$R^1$ is a member selected from the group consisting of $R^3$ (alkyl), $C(O)OR^3$ (alkoxycarbonyl), $NH(CO)R^3$ (alkylaminocarbonyl), $S(O)_2R^3$ (alkylsulfonyl), $S(O)_2R^4$ (phenylsulfonyl), $S(O)R^3$ (alkylsulfinyl), $P(O)_2R^3$ (alkylphosphonyl), $C(O)R^3$ (alkanoyl), and phenyl, wherein phenyl groups may be $C_1$ to $C_6$ alkyl substituted;

$R^2$ is H or $C_1$ to $C_6$ branched or straight chained alkyl;

$R^3$ is a straight or branched chain $C_4$ to $C_{12}$ alkyl group; and $R^4$ is phenyl or $C_1$ to $C_6$ alkyl substituted phenyl.

In the carbon chains described above, any integer within the described range may be used. For example, the phenyl group in $R^1$ may be substituted with a branched or straight chain $C_1$, $C_2$, $C_3$, $C_4$, $C_5$, or $C_6$ alkyl group; $R^2$ may be a branched or straight chain $C_1$, $C_2$, $C_3$, $C_4$, $C_5$, or $C_6$ alkyl group; $R^3$ may be a branched or straight chain $C_1$, $C_2$, $C_3$, $C_4$, $C_5$, $C_6$, $C_7$, $C_8$, $C_9$, $C_{10}$, $C_{11}$, or $C_{12}$ alkyl group; and $R^4$ may be a $C_1$, $C_2$, $C_3$, $C_4$, $C_5$, or $C_6$ alkyl (straight or branched) substituted phenyl.

These compounds are substituted analogs of kanamycin A. The present invention also relates to methods for the synthesis of such analogs and the utilization of them as antifungal agents.

Referring now to the invention in more detail, in Formula I there is shown the structure of the compounds related to the present invention. The compounds related to the present invention are analogs of parent molecule kanamycin A. The structure related to the present invention is distinguished from the parent molecule kanamycin A by the presence of functional groups terminating in either an alkyl or phenyl group in the 6 position of ring III.

More specifically, in reference to Formula I, the functional groups at the 6 position of ring III are identified as $XR^1$ wherein X is a member selected from the group consisting of O, S, and $NR^2$, where $R^2$ is H or $C_1$ to $C_6$ alkyl and $R^1$ is a member selected from the group consisting of $R^3$ (alkyl), $C(O)OR^3$ (alkoxycarbonyl), $NH(CO)R^3$ (alkylaminocarbonyl), $S(O)_2R^3$ (alkylsulfonyl), $S(O)_2R^4$ (phenylsulfonyl), $S(O)R^3$ (alkylsulfinyl), $P(O)_2R^3$ (alkylphosphonyl), $C(O)R^3$ (alkanoyl), and phenyl, wherein phenyl groups may be $C_1$ to $C_6$ alkyl substituted; $R^2$ is H or $C_1$ to $C_6$ branched or straight chained alkyl; $R^3$ is a straight or branched chain $C_4$ to $C_{12}$ alkyl group; and $R^4$ is phenyl or $C_1$ to $C_6$ alkyl substituted phenyl. Unless otherwise designated $R_3$ is preferable n-alkyl.

In more preferred embodiments X is O or S with O being particularly preferred, but can also be $NR^2$ with $R^2$ being preferably H. $R^1$ is preferably a member selected from the group consisting of $C(O)OR^3$ (alkoxycarbonyl), $S(O)_2R^3$ (alkylsulfonyl), $S(O)_2R^4$ (phenylsulfonyl), and $C_4$ to $C_{12}$ straight or branched chain alkyl. $R^3$ is also $C_4$ to $C_{12}$ straight or branch chain alkyl. $R^4$ is phenyl or $C_1$ to $C_6$ alkyl substituted phenyl. When X is S or $NR^2$, $R^1$ is $C_4$ to $C_{12}$ straight or branch chain alkyl.

In embodiments, the aminoglycosides may be used as illustrated above, as salts, or any other suitable form for delivery to a target organism.

C. Azoles

The aminoglycosides as described above and as set forth in Formula I may be combined with one or more of suitable azole. Azoles include compounds having a five-membered nitrogen heterocyclic ring containing at least one other non-carbon atom of either nitrogen, sulfur, or oxygen, such as azoles that include 1 nitrogen atom, 2 or more nitrogen atoms, 1 nitrogen atom and 1 oxygen atom, and 1 nitrogen atom and 1 sulfur atom. The five-membered nitrogen heterocyclic ring may be additionally substituted.

In some embodiments where the compounds are employed for biocidal or antibiotic effects, suitable azoles include those that have at least some desired biocidal effect. Exemplary azoles include pyrroles, pyrazoles, imidazoles, triazoles, tetrazoles, pentazoles, oxazoles, isoxazoles, thiazoles, and isothiazoles.

In some embodiments, the azole may be selected from one or more of the following: itraconazole, fluconazole, voriconazole, posaconazole, chlotrimazole, tioconazole, ketoconazole, metconazole, tebuconazole, and pyraclostrobin.

In embodiments, the azoles may be used as illustrated above, as salts, or any other suitable form for delivery to a target organism.

D. Combinations

The aminoglycosides and azoles may be used in any suitable ratio or combination. The ratio of azole to aminoglycoside may be from about 1:1 to about 1:1000, from about 1:5 to about 1:600, from about 1:20 to about 1:500, from about 1:30 to about 1:200, and from about 1:50 to about 1:100. For example, in some embodiments, the ratio of azole:aminoglycoside may be about 1:5, 1:21, 1:32, 1:53, 1:180, and 1:533.

One preferred embodiment of the present invention is the treatment of fungal infection in a host in need thereof, where the elimination or reduction of bacteria associated with said host is undesirable. Without wishing to limit the scope of the invention in any way, one such use could occur in human or non-human mammals, where treatment of a fungal infection with and aminoglycoside of the invention such as K20 would eliminate or alleviate the fungal infection, but not affect the integrity of the intestinal flora of the host. Again, without limiting the invention, a second example is the treatment or prevention of fungal disease in a host crop, where it is undesirable to affect the diversity or abundance of bacteria of said host crop.

In broad embodiment, the present invention is drawn to novel antifungal compounds, a method to synthesize said novel antifungal compounds, and methods to use said novel antifungal compounds to treat humans, animals, soil, or plants to eliminate fungal growth and activity. In one broad embodiment, the structure related to the present invention is derived from a parent aminoglycoside molecule other than kanamycin A that is capable of being modified by the addition of a variety of substituents on ring III equivalent of the ring III of kanamycin A. Particularly preferred is the addition of a carbon alkyl chain as designated herein on ring III.

In yet another broad embodiment the present invention is derived from the parent aminoglycoside molecule by the synthesis method shown herein, but the substituent, such as the carbon alkyl chain on ring III of the structure related to the present invention varies in the number of carbon atoms and hydrogen atoms.

In still yet another broad embodiment, the present invention is used to treat a variety of fungal pathogens related to human, crop, or animal disease.

In further broad embodiments, the compound of the present invention is administered by spraying, direct injection, topical application, ingestion (including pharmaceutical compositions that include the structure related to the present invention), or by inclusion in the water supply, to either a human, an animal, or a crop immediately threatened by, or potentially threatened by, a fungal pathogen, where fungal pathogen is causing or may cause fungal disease, and administration of the compounds of the present invention will reduce, eliminate, or avoid fungal disease.

EXAMPLES

The following examples are illustrative only and are not intended to limit the disclosure in any way. The following materials and methods were used in either one or more of the examples listed below. Further materials and methods are provided in the description of each example.

Aminoglycosides

All aminoglycosides were provided by the laboratory of Dr. Cheng-Wei T. Chang (Department of Chemistry and Biochemistry, Utah State University). For antifungal tests, stock solutions were prepared as 10 mg mL$^{-1}$ solutions in water and stored at minus 20.

Fungal Growth Media

PDB-CA and PDA-CA growth media were used throughout. However, in embodiments RPMI 1640, or any other suitable growth media, may be used.

Bacterial and Fungal Organisms

*Escherichia coli*

TGI, *Escherichia coli* B, *Staphylococcus aureus* ATCC 6538, *Micrococcus luteus*, and *Candida albicans* ATCC 10231 were obtained from the American Type Culture Collection (Manassas, Va., USA). *Fusarium graminearum* strain B-4-5A was obtained from the Small Grain Pathology Program, University of Minnesota, Minneapolis Minn., USA. *Saccharomyces cerevisiae* W303C and *Rhodotorula pilimanae* were obtained from Dr. J. Y. Takemoto, Utah State University, Logan, Utah, USA). *Aspergillus flavus, Fusarium oxysporum, Fusarium culmorum, Microdochium nivale, Mucor haemalis, Ulocladium* spp., *Penicillium* spp., *Rhizopus stolonifer* and *Cladosporium cladosporioides* were obtained from Dr. B. Kropp (Utah State University, Logan, Utah, USA) and *Aspergillus niger* was obtained from Dr. C. Nischwitz (Utah State University, Logan, Utah, USA). Filamentous fungi and yeasts were cultivated at 35° C. in PDB-CA. Bacterial strains were grown at 37° C. for 24 h on Luria-Bertani medium (14) except for *Staphylococcus aureus* ATCC6538 which was grown on Mueller-Hinton medium (Difco, B D, Franklin Lakes, N.J., USA).

Procedures for In Vitro Antifungal Tests

In vitro antifungal activities were determined by the general methods of the Clinical and Laboratory Standards Institute (NCCLS. Reference method for broth dilution antifungal susceptibility testing of filamentous fungi. Approved standard M38-A (National Committee for Clinical Laboratory Standards, Wayne, Pa., 2002)). For MIC tests, *Fusarium graminearum, Rhodotorula pilimanae*, and *Aspergillus flavus* were grown in PDB-CA medium for 48 h at 28° C. with aerobic shaking For disk diffusion growth inhibitory assays, various fungal species were inoculated in the middle of PDA-CA medium plate surfaces. Sterilized paper disks (0.5 cm diameter) were placed on the inoculated agar medium surfaces equidistant and around the fungal inoculum. Eight µL aliquots of test solutions (10 mg mL$^{-1}$) were applied to the disks, and the plates were incubated for 24 to 48 h at 28° C. before examination of the inhibition patterns seen as cleared zones of growth inhibition surrounding the disks. Assays for determination of MICs were conducted in sterile, flat-bottomed 96-well microtiter plates (Corning Costar, Corning, N.Y.) in the range of 500 to 1 µg mL$^{-1}$. Stock solutions of analogs were prepared at concentrations of 2 mg mL$^{-1}$ in water. In microtiter plates, 50 µL aliquots of stock solutions were added in the third column and 10 consecutive two-fold serial dilutions were made in each row with sterile distilled water. Then, 40 µL of PDB-CA medium and 10 µL aliquots of a 100,000 macroconidia per mL fungal suspension were added to each well. Negative (90 µL of growth medium and 10 µL of water) and positive (90 µL of growth medium and 10 µL of culture or macroconidia) controls were placed in separate wells. The microtiter plates were incubated at 28° C. and visually inspected and scored every 24 h. Microbroth dilution assays in a single MIC test were replicated three times, and each test repeated at least twice.

Example 1

6"-O-octanesulfonylkanamycin A (K20)

In reference to FIG. 1, Tetra-Boc protected kanamycin (B4K) can be prepared with reported method (J. Med. Chem. 1991, 34, 1468-1476). A solution of B4K (90 g), octanesulfonyl chloride (64 mL) in anhydrous pyridine (800 mL) was stirred at 0° C. overnight allowing the temperature to warm up to room temperature. The clear brownish mixture was stirred for another 6 days at room temperature and one day at 40° C., and then concentrated to an oily crude product. Water (500 mL) was added and the mixture was stirred for another day. The mixture was transferred to a reparatory funnel with more water and EtOAc (2 L). The organic layer was washed with 0.5 N HCl$_{(aq)}$ (×2) and water. The washing sequence was repeated 3-4 times. If solid precipitation (mostly unreacted B4K) occurred, the organic layer was filtered first to remove the solid. After completion of the washing, the EtOAc solution was filtered through a Frit funnel and the EtOAC was evaporated. The brownish crude product was treated with a solution of TFA/DCM (¼) (200 mL). After being stirred overnight, the solvents were removed. Water was added and evaporated to ensure the removal of residual acid. The crude product was dissolved in water and washed with EtOAc until the color in EtOAc was clear. The aqueous solution was evaporated and passed through a column packed with Dowex1X-8 (Cl- form). After removal of solvent, the desired K20 was afforded as a yellowish solid.

Other K20 analogs, i.e. K05, K07, K17, K18, K19 and K22 can be prepared in a similar manner using appropriate reactants in the place of octanesulfonyl chloride.

Example 2

Relative Growth Inhibitory Activities of K20 Against Bacteria and Fungal Species Referring now to Table 1 there is shown the relative growth inhibitory activities of K20 against various species of bacteria and fungi as determined by disk diffusion agar plate assays.

TABLE 1

Growth inhibitory activities of K20 and kanamycin A against bacteria and fungi

| Organisms | [a]Relative Activity | |
|---|---|---|
| | K20 | kanamycin A |
| Bacteria | | |
| Escherichia coli TG1 | --- | +++ |
| Staphylococcus aureus ATCC 6538 | --- | +++ |
| Micrococcus luteus | -- | +++ |
| Filamentous fungi | | |
| Fusarium graminearum | [b]+++ | --- |
| Fusarium oxysporum | ++ | --- |
| Fusarium culmorum | +++ | [c]nd |
| Microdochium nivale | +++ | nd |
| Mucor haemalis | +++ | --- |
| Ulocladium spp. | +++ | --- |
| Penicillium spp | ++ | nd |
| Rhizopus stolonifer | +++ | --- |
| Cladosporium cladosporioides | ++ | nd |
| Yeasts | | |
| Rhodotorula piliminae | +++ | --- |
| Candida albicans ATCC 10231 | ++ | --- |
| Saccharomyces cerevisiae W303C | ++ | --- |

[a]Determined by measurement of zone of inhibition diameters in disk diffusion growth inhibitory assays in PDA-CA medium
[b]+++, considerable activity; ++, moderate activity; ---, no activity
[c]nd, not determined Of considerable importance is the activity shown against *Fusarium graminarum*. *Fusarium graminarum* is a fungus that infects wheat and the disease is also known as head scab or *Fusarium* Head Blight and is a serious deterrent to the harvesting of good quality wheat and often results in farmers being forced to discard their crop. Consistent with the disk diffusion assay data shown in Table 1, the MIC testing of K20 against *Fusarium graminarum* resulted in MIC's of between 7.8 and 15.6 µg mL$^{-1}$ using PDB-CA growth medium.

Example 3

Antifungal Activities of K20 Analogues Against *Fusarium graminearum* and/or *Rhodotorula pilimanae*

Referring now to Table 2 there is shown the relative growth inhibitory activities of K20 analogues against *Fusarium graminearum* and/or *Rhodotorula pilimanae* as determined by MIC assays or disk diffusion agar plate assays.

TABLE 2

Activities of other K compounds

| Code | Structure | MIC (microgram/mL) | Remark |
|---|---|---|---|
| K05 | [structure image] | growth inhibition >62.5 ug/mL no pigmentation 31.25 ug/mL against *Fusarium graminearum* | |
| K07 | [structure image] | | Similar to K05 |

TABLE 2-continued

Activities of other K compounds

| Code | Structure | MIC (microgram/mL) | Remark |
|---|---|---|---|
| K17 | (structure) | Not determined. Only inhibition zone assay and not active against *Rhodotorula pilimanae* | The yield is very low. |
| K18 | (structure) | 15.6 ug/mL against *Fusarium graminearum* 62.5 ug/mL against *Rhodotorula pilimanae* | The yield is very low. |
| K19 | (structure) | relatively little but nevertheless some inhibition of *Rhodotorula* | |
| K22 | (structure) | 31.3 ug/mL against *Fusarium graminearum* | |

The alkylsulfonyl, alkylcarbonyl, and alkylthio derivatives of kanamycin A were shown to be more active than the alkylamino and toluene (p-methylphenyl) derivatives that, nevertheless, show some antifungal activity.

Example 4

Selective Antimicrobial Activity of K20

The MICs of K20 were determined for selected bacterial pathogens. For purposes of the experiments discussed in this paragraph, the MIC is defined as the lowest concentration of compound needed to inhibit the growth of bacteria. A solution of a selected bacterium was inoculated into trypticase soy broth (Difco, B D, Franklin Lakes, N.J., USA), at 35° C. and incubated for 1-2 hours. Following incubation, the bacterial concentrations were determined, and diluted with broth, if necessary, to an absorption value of 0.08 to 0.1 at 625 nm. The adjusted inoculated medium (100 L) was diluted with 10 mL broth, and then applied to a 96-well microtiter plate (50 L). A series of solutions (50 L each in 2-fold dilution) of K20 was added to the testing wells. The 96-well plate was incubated at 35° C. for 12-18 hrs. The MIC tests were repeated at least three times. MIC values ($\mu g$ $mL^{-1}$) for K20 were 250 for *Escherichia coli* B and 62.5 for *Micrococcus luteus*. Corresponding MIC values for kanamycin A and B were 0.98 $\mu g$ $mL^{-1}$ for *Micrococcus luteus* and 1.95 $\mu g$ $mL^{-1}$ for *Escherichia coli* B. The bacterial MIC values determined for K20 exceed the values that typically prompt consideration of candidate compounds as effective antibacterial antibiotics (<16 $\mu g$ $mL^{-1}$) whereas MIC values for kanamycin A and B demonstrated effective antibacterial activity.

In summary, the aminoglycoside analogs of the present invention demonstrate insufficient or no antibacterial activity and are structurally distinct from kanamycin A due to the presence of a carbon alkyl chain or aryl ring on ring III. The carbon alkyl chain or aryl ring on ring III, absent on the parent molecule kanamycin A, is the structural feature of the present invention most likely responsible for the novel antifungal activity of the present invention. The fungal specificity of the present invention will benefit crop protection strategies because use of the present invention will not promote bacterial resistance, whereas conventional aminoglycosides do promote bacterial resistance.

Example 5

Disk Diffusion Tests to Determine Synergistic Inhibition of Azole-resistant *Candida albicans* ATCC 10231 by Itraconazole and K20

Figure 2:
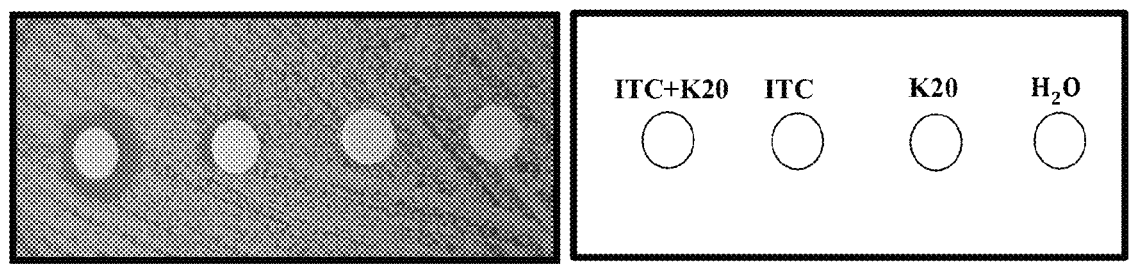
FIG. 2 illustrates itraconazole and K20 synergistic inhibition of *Candida albicans* ATCC 10231

Method: In vitro antifungal activities determined by disk diffusion growth inhibitory assays were determined by methods recommended by the Clinical and Laboratory Standards Institute[2,3]. *Candida albicans* ATCC 10231 yeast cells were grown in PDB-CA medium for 48 h at 30° C. with aerobic shaking. The culture densities were adjusted to ~5×10⁵ c.f.u. $mL^{-1}$, and the fungal cultures were spread-plated on PDB-CA agar plate medium surfaces. Sterilized paper disks (0.5 cm diameter) were placed on the inoculated agar medium surfaces. As shown in FIG. 2, 10 $\mu L$ of itraconazole (ITC)+K20 (0.5+32 $\mu g$/mL), ITC (0.5 $\mu g$/mL), K20 (32 $\mu g$/mL) and distilled water were applied to the disks (left to right, respectively). The plates were incubated for 24 to 48 h at optimal growth temperature (30° C.) before examination and measurement of the diameters of the cleared zones of inhibition observed for growth inhibition.

Results: Zone of growth inhibition was visible with the ITC+K20 combination only (FIG. 2) indicating synergistic fungicidal activity. ITC and K20 alone at 0.5 $\mu g$ $mL^{-1}$ and 32 $\mu g$ $mL^{-1}$ per disc had no fungicidal activities.

Example 6

Checkerboard Assay to Determine Synergistic Inhibition of Azole-resistant *Candida albicans* ATCC 10231 by Azoles and K20

Method: The interactions between K20 and azoles against azole-resistant *C. albicans* ATCC 10231 were tested using a microdilution checkerboard technique according to CLSI M27-A guidelines for yeasts. Synergistic interactions were performed using 96-well flat-bottomed microtiter plates. The *C. albicans* ATCC 10231 inoculum was at a viable cell density of 1×10⁵ c.f.u $mL^{-1}$ as determined by viable cell colony counting on agar plates. The final concentrations of the drugs ranged from 0.04 to 3 $\mu g$ $mL^{-1}$ for itraconazole (ITC); 0.3 to 48 $\mu g$ $mL^{-1}$ for fluconazole (FLC); 0.01 to 1 $\mu g$ $mL^{-1}$ for voriconazole (VRZ); 0.07 to 2.5 $\mu g$ $mL^{-1}$ for metconazole; 0.04 to 3 $\mu g$ $mL^{-1}$ for pyraclostrobin; 0.07 to 2.5 $\mu g$ $mL^{-1}$ for chlotrimazole; 0.005 to 0.5 $\mu g$ $mL^{-1}$ for tioconazole; 0.005 to 2 $\mu g$ $mL{-1}$ for posaconazole; 0.3 to 24 $\mu g$ $mL^{-1}$ for ketoconazole and 2 to 256 $\mu g$ $mL^{-1}$ for K20.

In microtiter plates, 50 $\mu L$ aliquots of stock solutions of K20 were added in the ninth column and 8 consecutive two-fold serial dilutions were made in each row with sterile distilled water. Similarly, 100 uL aliquots of stock solutions of azoles were added in the eighth row and 8 consecutive two-fold serial dilutions were made in each column mixing with K20 and sterile distilled water. In this way, all azoles standards dilutions were mixed with the appropriate concentration of K20 compounds thus obtaining a series of the combinations of azoles and K20 compounds. Then, 90 $\mu L$ of PDB-CA growth medium and 10 $\mu L$ of fungal culture was added to each well. Negative (190 $\mu l$ of growth medium and 10 $\mu L$ of water) and positive (190 $\mu L$ of growth medium and 10 $\mu L$ of organism) controls were placed in separate wells. The plates were incubated at room temperature or 30° C. and visually inspected and scored every 24 to 48 h. Checkerboard microbroth dilution assays in a single test were replicated three times, and each test repeated at least twice. The analysis of the combination of K20 and azoles was obtained by calculating the Fractional Inhibitory Concentration Index (FICI) as follows: FICI=(MIC drug A combination/MIC drug A alone)+(MIC drug B combination/MIC drug B alone). Drug interactions were classified as synergistic, indifferent, or antagonistic according to the fractional inhibitory concentration index (FICI). The interaction was defined as synergistic if the FICI was ≤0.5, indifferent if >0.5 but <4.0, and antagonistic if >4.0.

Results: (Summarized in Table 3). The minimal inhibitory concentration (MIC) values for azoles and K20 ranged from 0.25-48 $\mu g$ $mL^{-1}$ and 128 $\mu g$ $mL^{-1}$, respectively against *C. albicans* 10231. Similarly, the in vitro interactions of azoles and K20 showed synergistic effect against *C. albicans* 10231 with FICI values ranging between 0.12-0.31.

TABLE 3

Azole-resistant *Candida albicans* ATCC10231 synergistic inhibition by K20 - azole combinations

| | MIC ($\mu g\ mL^{-1}$) | | | | | |
|---|---|---|---|---|---|---|
| | Alone | | In Combination | | | |
| | Azole | K20 | Azole | K20 | FICI | Effect |
| itraconazole | >3 | 128 | 0.18 | 32 | 0.31 | synergy |
| fluconazole | >24 | 128 | 3 | 16 | 0.18 | synergy |
| voriconazole | >1 | 128 | 0.125 | 4 | 0.15 | synergy |
| posaconazole | >0.75 | 128 | 0.09 | 16 | 0.24 | synergy |
| chlotrimazole | 1.25 | 128 | 0.15 | 8 | 0.18 | synergy |
| tioconazole | 0.25 | 128 | 0.03 | 16 | 0.25 | synergy |
| ketoconazole | 24 | 128 | 1.5 | 32 | 0.31 | synergy |
| metconazole | 2.5 | 128 | 0.15 | 8 | 0.12 | synergy |
| pyraclostrobin | 6 | 128 | 0.75 | 16 | 0.25 | synergy |

Example 7

Time-kill Curves to Observe Synergistic Interaction of Itraconazole and K20 Against Azole-Resistant *Candida albicans* ATCC 10231 Growing in PDB-CA Medium Method: Strain *Candida albicans* ATCC 10231 was prepared at an inoculum size of $10^5$ c.f.u. $mL^{-1}$ in PDB-CA medium. The drug concentrations used were 32 $\mu g\ mL^{-1}$ for K20 and 0.18 $\mu g\ mL^{-1}$ for itraconazole. At designated times (0, 3, 6, 9, 24 and 48 h after incubation), 100 $\mu L$ aliquots were removed from each solution and serially diluted 10-fold in sterile water. One hundred $\mu L$ volumes of each dilution were streaked on agar surfaces of potato dextrose agar plates to allow growth. Colony counts were determined after incubation for 48 h. The experiment was performed triplicate. For antifungal drug combination interaction assessment, the following criteria were applied: (i) "synergy" is defined as a $\geq 2$ log 10 decrease in c.f.u. $mL^{-1}$ compared to the most active constituent; and (ii) "antagonism" is defined as a $\geq 2$ log 10 increase in c.f.u. $mL^{-1}$ compared to the least active agent.

Results: The synergistic interaction of itraconazole and K20 was confirmed by time kill curves against *Candida albicans* ATCC 10231 (FIG. 2). Combinations of itraconazole and K20 at 0.18+32 $\mu g\ mL^{-1}$, respectively (open squares, □) and at 0.37+32 $\mu g\ mL^{-1}$, respectively (closed circles, ●) yielded a $\geq 2$ log 10 decrease in c.f.u. $mL^{-1}$ compared with 0.18 and 0.37 $\mu g\ mL^{-1}$ itraconazole (closed triangle, ▲, and cross, ×, respectively) and 32 $\mu g\ mL^{-1}$ K20 (open diamonds, ◊) alone. The effect of 32 $\mu g\ mL^{-1}$ K20 alone was the same as the control with no added compound (closed squares, ■).

Example 8

Cytotoxicity of Mixtures of Itraconazole and K20 on Chinese Hamster Ovary Cells

Method: Chinese Hamster Ovary (CHO) cells (line 1-15) were maintained and suspended in HyCell CHO Growth Medium (Thermo Fisher Scientific) at approximately 50-100 rpm in reciprocal shaking flasks for 48 h under standard animal cell culture conditions (5% $CO_2$, 37° C.). The cells were transferred into sterile 50 mL Falcon conical plastic tubes containing 10 mL of the medium at a cell density of $2.5\times10^5$ cells $mL^{-1}$. Different combination mixtures of itraconazole and K20 at final concentration ratios ([itraconazole]:[K20] ($\mu g\ mL^{-1}$)) of 0.18:32, 0.37:16, 0.9:160 and 3.7:80, and itraconazole alone (3.7 $\mu g\ mL^{-1}$), K20 alone (160 $\mu g\ mL^{-1}$), and an equivalent volume of sterile double distilled water (untreated control) were added separately to the suspended cells. The suspensions were incubated with continuous agitation for 48 h at 37° C. with 5% $CO_2$ in a humidified incubator. After 24 and 48 h, lmL portions of the cell culture suspensions (drug treated or untreated) were transferred to Beckman Coulter Vi-Cell XR cups and mixed with Trypan Blue to determine cell counts and viability in a Beckman Coulter Vi-Cell counter.

Figure 3:
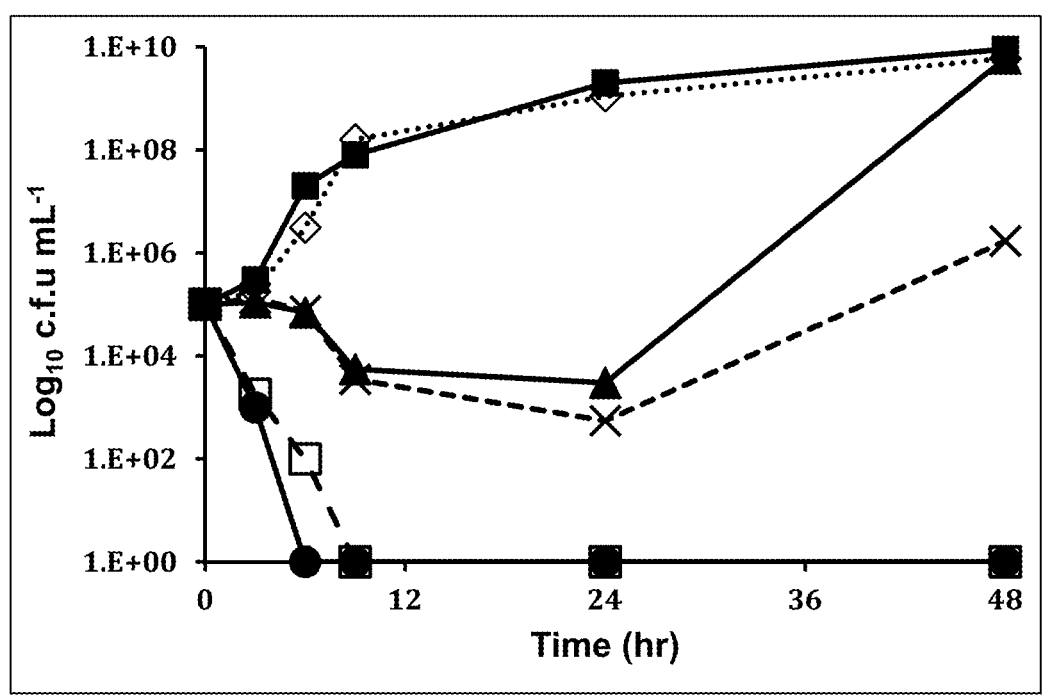
FIG. 3 illustrates the time kill curves of itraconazole and K20 synergistic inhibition of *Candida albicans* ATCC 10231.
Figure 4:
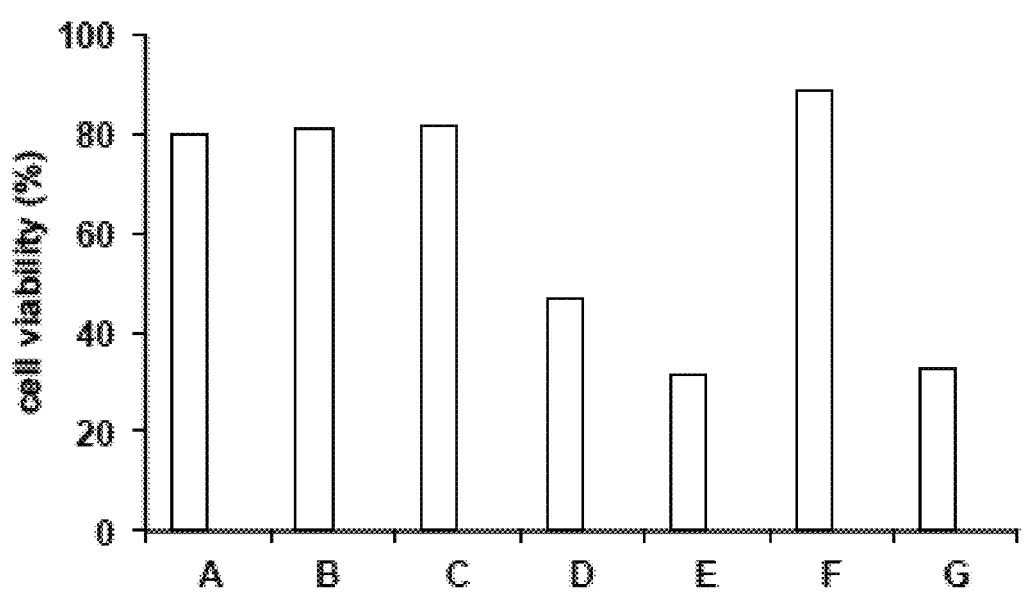
FIG. 4 illustrates cytotoxicity of itraconazole and K20 mixtures on Chinese Hamster Ovary (CHO) cells

Results and Conclusions: Mixtures of itraconazole and K20 that give optimal antifungal FICIs (e.g. 0.18:32 and 0.37:16 for [itraconazole]:[K20] ($\mu g\ mL^{-1}$) showed no toxicity effects against CHO cells when compared to untreated controls (FIG. 3). However, 38% and 63% decreases in viability were observed with [itraconzole]:[K20] ($\mu g\ mL^{-1}$) ratios of 0.9:160 and 3.7: 80, respectively. K20 alone at 160 $\mu g\ mL^{-1}$ was not toxic and showed viability rates comparable to those of untreated controls. Itraconazole alone at 3.7 $\mu g\ mL^{-1}$ decreased cell viability 63%. The results show that itraconazole: K20 combination mixtures showing optimal FICIs and at drug concentrations having the lowest FIC values are not toxic to CHO cells. Also, K20 is not toxic to CHO cells at concentrations that exceed its MICs (up to 160 $\mu g\ mL^{-1}$) whereas itraconazole is toxic to these cells at concentrations that are 5 to fold higher than its MICs. The data shown in FIG. 3 may be described as follows: Bars represent degree of cell viability with: no drug treatment (control) (A), treatment with K20 (160 $\mu g\ mL^{-1}$) (F) and itraconazole (3.7 $\mu g\ mL^{-1}$) (G), and with combinations of itraconazole and K20 at [itraconazole]:[K20] ($\mu g\ mL^{-1}$) ratios of 0.18:32 (C), 0.37:16 (D), 0.9:160 (E), and 3.7/80 (F).

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention as claimed. Such embodiments may encompass different means of applying the compounds of the present invention, including, but not limited to, spraying, topical application, or injection. Various embodiments may also include the treatment different kinds of hosts susceptible to fungal infections. Types of hosts can include, but are not limited to, warm-blooded animals (including humans and other mammals), plants, fish, or bacterial cultures.

It will be appreciated that various of the above-disclosed and other features and functions, or alternatives thereof, may be desirably combined into many other different systems or applications. Also, various presently unforeseen or unanticipated alternatives, modifications, variations or improvements therein may be subsequently made by those skilled in the art, and are also intended to be encompassed by the following claims.

What is claimed is:

1. A fungicidal composition comprising:
   an aminoglycoside compound, or salt thereof having the formula:

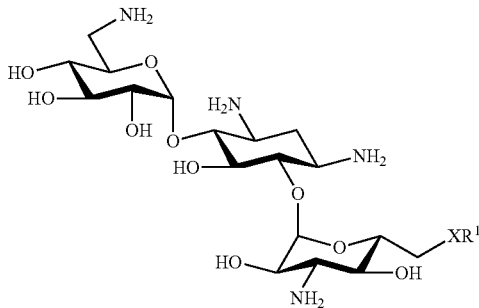

wherein:
   X is a member selected from the group consisting of O and S;
   $R^1$ is a member selected from the group consisting of $R^3$, $C(O)OR^3$, $S(O)_2R^3$, $S(O)_2R^4$, $S(O)R^3$, $P(O)_2R^3$, and phenyl, wherein phenyl groups may be $C_1$ to $C_6$ alkyl substituted;
   $R^3$ is a straight or branched chain $C_6$ to $C_{12}$ alkyl group; and
   $R^4$ is phenyl or $C_1$ to $C_6$ alkyl substituted phenyl; and
   an azole.

2. The composition according to claim 1, wherein:
   X is O or S;
   $R^1$ is a member selected from the group consisting of $S(O)_2R^3$ and $S(O)_2R^4$,
      wherein:
      $R^3$ is $C_6$ to $C_{12}$ straight or branched chain alkyl and
      $R^4$ is phenyl or $C_1$ to $C_6$ alkyl substituted phenyl.

3. The composition according to claim 1, wherein $R^1$ is $C(O)OR^3$.

4. The composition according to claim 1, wherein $R^1$ is $S(O)R^3$.

5. The composition according to claim 1, wherein $R^1$ is $P(O)_2R^3$.

6. The composition according to claim 2, wherein X is O and $R^1$ is $S(O)_2R^3$.

7. The composition according to claim 6, wherein $R^3$ is $C_6H_{13}$.

8. The composition according to claim 6, wherein $R^3$ is $C_8H_{17}$.

9. The composition according to claim 2, wherein X is O and $R^1$ is $S(O)_2R^4$.

10. The composition according to claim 9, wherein $R^4$ is p-tolyl.

11. The composition according to claim 2, wherein X is S and $R^1$ is $R^3$.

12. The composition according to claim 11, wherein $R^3$ is $C_8H_{17}$.

13. The composition according to claim 1, wherein the azole is selected from the group consisting of itraconazol, fluconazole, voriconazole, posaconazole, clotrimazol, tioconazole, ketoconazole, metconazole, tebuconazole, and pyraclostrobin.

14. A method of treating a fungal infection which comprises administering to a host in need thereof an effective amount of a fungicidal composition comprising:
   an aminoglycoside compound, or salt thereof having the formula:

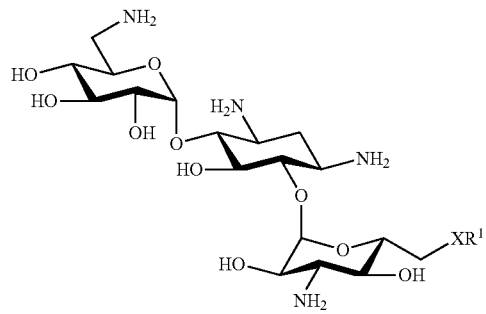

wherein:
   X is a member selected from the group consisting of O and S;
   $R^1$ is a member selected from the group consisting of $R^3$, $C(O)OR^3$, $S(O)_2R^3$, $S(O)_2R^4$, $S(O)R^3$, $P(O)_2R^3$, and phenyl, wherein phenyl groups may be $C_1$ to $C_6$ alkyl substituted;
   $R^3$ is a straight or branched chain $C_6$ to $C_{12}$ alkyl group; and
   an azole.

15. The method according to claim 14 wherein:
   X is O or S;
   $R^1$ is a member selected from the group consisting of $S(O)_2R^3$ and $S(O)_2R^4$,
   $R^3$ is $C_6$ to $C_{12}$ straight or branched chain alkyl, and
   $R^4$ is phenyl or $C_1$ to $C_6$ alkyl substituted phenyl.

16. The method according to claim 15 wherein X is O and $R^1$ is $S(O)_2R^3$.

17. The method according to claim 16 wherein $R^3$ is $C_6H_{13}$.

18. The method according to claim 16 wherein $R^3$ is $C_8H_{17}$.

19. The method according to claim 14 wherein said host in need thereof is a plant or an animal.

20. The method of claim 14, wherein the azole is selected from the group consisting of itraconazole, fluconazole, voriconazole, posaconazole, clotrimazole, tioconazole, ketoconazole, metconazole, tebuconazole, and pyraclostrobin.

* * * * *